United States Patent
Derry et al.

(10) Patent No.: US 10,857,704 B2
(45) Date of Patent: *Dec. 8, 2020

(54) EYELET FOR BIOMEDICAL ELECTRODE AND PROCESS FOR PRODUCTION THEREOF

(71) Applicant: 3M INNOVATIVE PROPERTIES COMPANY, Saint Paul, MN (US)

(72) Inventors: Cameron E. Derry, London (CA); John P. Tryphonopoulos, London (CA)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/834,004

(22) Filed: Mar. 30, 2020

(65) Prior Publication Data

US 2020/0223110 A1 Jul. 16, 2020

Related U.S. Application Data

(63) Continuation of application No. 16/063,397, filed as application No. PCT/US2016/063948 on Nov. 29, 2016, now Pat. No. 10,639,827.

(Continued)

(51) Int. Cl.
*B29C 43/00* (2006.01)
*A61B 5/00* (2006.01)
(Continued)

(52) U.S. Cl.
CPC .......... *B29C 43/222* (2013.01); *A61B 5/0408* (2013.01); *B29C 43/24* (2013.01);
(Continued)

(58) Field of Classification Search
None
See application file for complete search history.

(56) References Cited

U.S. PATENT DOCUMENTS

| 3,834,373 A | 9/1974 | Sato |
| 3,976,055 A | 8/1976 | Monter |

(Continued)

FOREIGN PATENT DOCUMENTS

| CA | 2585355 | 10/2005 |
| CN | 203636902 | 6/2014 |

(Continued)

OTHER PUBLICATIONS

International Search Report for PCT/US2015/064920 dated Mar. 16, 2017.

(Continued)

*Primary Examiner* — Linda L Gray (57) ABSTRACT

A process for producing an eyelet for a biomedical electrode (e.g. an electrocardiogram (ECG) electrode) involves: hot pressing an electrically conductive thermoplastic or elastomeric resin to produce a film having a web of eyelets, each eyelet having a post protruding from a first face of the film and a flange at a second face of the film; applying a coating of a non-polarizable conductive material (e.g. a silver-containing material) on to a contact face of the flange; and, cutting the film to produce the eyelets separated from the web. Preferably, the process involves extrusion replication. A web of eyelets for biomedical electrodes has a film of an electrically conductive thermoplastic or elastomeric resin possessing a plurality of posts protruding from a first face of the film, and preferably a layer of a non-polarizable conductive material on a second face of the film. The process may be a one-step continuous process that is cheaper and simpler than current commercial processes.

8 Claims, 3 Drawing Sheets

Related U.S. Application Data (60) Provisional application No. 62/270,672, filed on Dec. 22, 2015.

(51) Int. Cl.

| | | |
|---|---|---|
| *B29C 43/22* | (2006.01) | |
| *A61B 5/0408* | (2006.01) | |
| *B29C 43/24* | (2006.01) | |
| *B29C 43/46* | (2006.01) | |
| B29C 43/32 | (2006.01) | |
| B29C 43/34 | (2006.01) | |
| A61B 5/0416 | (2006.01) | |
| B29C 43/44 | (2006.01) | |

(52) U.S. Cl.
CPC ............ *B29C 43/46* (2013.01); *A61B 5/0416* (2013.01); *A61B 2562/125* (2013.01); *B29C 43/22* (2013.01); *B29C 43/32* (2013.01); *B29C 43/34* (2013.01); *B29C 43/44* (2013.01); *B29C 2043/461* (2013.01); *B29C 2043/463* (2013.01); *B29C 2043/465* (2013.01); *B29C 2043/467* (2013.01); *Y10T 156/1084* (2015.01); *Y10T 156/1092* (2015.01); *Y10T 156/1093* (2015.01)

(56) References Cited

U.S. PATENT DOCUMENTS

| | | | |
|---|---|---|---|
| 4,377,170 | A | 3/1983 | Carim |
| 4,635,642 | A | 1/1987 | Cartmell |
| 4,727,881 | A | 3/1988 | Craighead |
| 4,848,348 | A | 7/1989 | Craighead |
| 4,938,219 | A | 7/1990 | Ishii |
| 5,406,945 | A | 4/1995 | Riazzi |
| 5,489,215 | A | 2/1996 | Wright |
| 5,782,761 | A | 7/1998 | Gusakov |
| 6,415,170 | B1 | 7/2002 | Loutis |
| 6,511,701 | B1 | 1/2003 | Divigalpitiya |
| 6,569,494 | B1 | 5/2003 | Chambers |
| 6,650,922 | B2 | 11/2003 | Kurata |
| 6,834,612 | B2 | 12/2004 | Chambers |
| 6,919,504 | B2 | 7/2005 | McCutcheon |
| 7,034,403 | B2 | 4/2006 | Divigalpitiya |
| 8,637,136 | B2 | 1/2014 | Ferguson |
| 9,192,313 | B1 | 11/2015 | Lisy |
| 2005/0261565 | A1 | 11/2005 | Lane |
| 2009/0253975 | A1 | 10/2009 | Tiegs |
| 2010/0159197 | A1 | 6/2010 | Ferguson |
| 2012/0309603 | A1 | 12/2012 | Seifert |
| 2013/0037987 | A1 | 2/2013 | Clarke |
| 2013/0085368 | A1 | 4/2013 | Coggins |

FOREIGN PATENT DOCUMENTS

| | | |
|---|---|---|
| EP | 0195859 | 10/1986 |
| EP | 0597156 | 5/1994 |
| WO | WO 84/02423 | 6/1984 |
| WO | WO 98/02088 | 1/1998 |
| WO | WO 02/089906 | 11/2002 |
| WO | WO 2011/106730 | 9/2011 |
| WO | WO 2013/049467 | 4/2013 |

OTHER PUBLICATIONS

International Search Report for PCT/US2015/063956 dated Mar. 6, 2017.
International Search Report for PCT/US2016/063948 dated Mar. 17, 2017.
"Conductive polymer" from Wikipedia, the free encyclopedia; Dec. 11, 2015; 6 pgs; available at https//web.archive org/web/20151211045601/ https://en.wikipedia org/wiki/Conductive_polymer (XP055347878).
"Poly(p-phenylene sulfide)" from Wikipedia, the free encyclopedia; May 8, 2015; available at https://web.archive.org/web/20150508022926/ http://en.wikipedia.org/wiki/Polyphenylene_sulfide (XP055347876).
"Ryton—Polyphenyl Sulfide, Polymer Plastics Company, LC, Carson City, Nevada;" Sep. 16, 2015; available at https://web.archive. org/web/20150916115247/http://www.polymerplastics.com/performance_ryton.shtml (XP055347872).

EYELET FOR BIOMEDICAL ELECTRODE AND PROCESS FOR PRODUCTION THEREOF

CROSS REFERENCE TO RELATED APPLICATIONS

This application is a continuation of U.S. application Ser. No. 16/063,397, filed Jun. 18, 2018, which is a national stage filing under 35 U.S.C. 371 of International Application No. PCT/US2016/063948, filed Nov. 29, 2016, which claims the benefit of U.S. Provisional Application No. 62/270,672, filed Dec. 22, 2015. The disclosures of all applications are incorporated by reference in their entirety herein.

This application relates to medical devices, in particular to medical electrodes, components thereof and methods of producing components of medical electrodes.

BACKGROUND

The basic function of a medical ECG electrode is to act as half a galvanic cell to convert ionic potential of the body into an electrical signal, which can be displayed as an output. Current biomedical electrodes use a silver coated eyelet in contact with an ionically conductive gel to trace the heartbeat signal. The eyelet is typically produced by injection molding either glass filled or carbon fiber filled ABS resin. This eyelet proceeds through many further steps before being coated with silver on the entire surface of the eyelet. This production method produces dimensionally stable eyelets but requires many steps due to the injection molding process. Additionally, due to the injection molding process the eyelets are produced and processed in a discrete manner. Due to this process, opting to selectively coat only one face of the eyelet instead of all surfaces with silver becomes difficult. This uniform coating is essential for glass filled eyelets to render them conductive, but not so if the eyelet is inherently conductive. Using current manufacturing processes it requires many steps to produce a finished eyelet.

SUMMARY

There remains a need for simpler processes for manufacturing eyelets for biomedical electrodes in fewer steps.

There is provided a process for producing an eyelet for a biomedical electrode, comprising: hot pressing an electrically conductive thermoplastic or elastomeric resin to produce a film comprising a web of eyelets, each eyelet comprising a post protruding from a first face of the film and a flange at a second face of the film; applying a coating of a non-polarizable conductive material on to a contact face of the flange; and, cutting the film to produce the eyelets separated from the web.

There is further provided a web of eyelets for biomedical electrodes, comprising: a film of an electrically conductive thermoplastic or elastomeric resin having a plurality of posts protruding from a first face of the film; and, a layer of a non-polarizable conductive material on a second face of the film.

There is further provided a web of eyelets comprising: a film of an electrically conductive thermoplastic or elastomeric resin having a plurality of eyelets formed therein, each eyelet comprising a post protruding from a first face of the film and a flange at a second face of the film.

There is further provided a biomedical electrode comprising an eyelet produced by the above described process or cut from the above described web of eyelets.

The process permits rapid and continuous production of eyelets having non-polarizable conductive material only on a contact face of the eyelet thereby decreasing cost and simplifying the production line. Further, the process permits thermally embedding the non-polarizable conductive material into the contact face increasing robustness of the non-polarizable conductive material layer, and can take advantage of heat from melt processed conductive resin to dry and sinter a printed silver ink layer opening ink printing as a viable method for applying the non-polarizable conductive material to the contact face of the eyelet. In one embodiment, the use of extrusion replication to form eyelet webs from conductive resins results in desired fiber orientations in resin matrix to provide better electrical conduction of the electrical signal as compared to conventional molding methods.

DETAILED DESCRIPTION

A fabrication method for producing 3-dimensional eyelet components for use in biomedical electrodes is provided. The eyelets may be extruded, formed, and coated with non-polarizable conductive material in fewer steps (e.g. one step) in a continuous manner, as compared to a traditional process which requires many steps. The process may be tailored to meet varying eyelet conductivity and size depending on required electrode performance.

The conductive thermoplastic or elastomeric resin may comprise any resin suitable for use in electrodes. The resin may comprise a thermoplastic resin, an elastomeric resin, copolymers thereof or any blend or mixture thereof. Some particular examples include polyolefin (e.g. polypropylene, such as low density polypropylene), polyacrylate, polyethylene terephthalate (PET), acrylonitrile-butadiene-styrene (ABS), poly(dimethylsiloxane) (PDMS), ethylene propylene diene monomer (EPDM) resin, and the like. The resin may comprise usual additives in the polymer industry. For use as in electrodes, it is desirable to confer electrical conductivity on the bulk of the resin by using inherently conductive polymers and/or by dispersing one or more electrically conductive fillers in a resin matrix. Some examples of inherently conductive polymers include doped polyolefins, polythiophenes, polypyrroles and the like. Some examples of electrically conductive fillers include metals (e.g. nickel, iron, and the like), conductive carbonaceous material (e.g. graphite, polyacrylonitrile (PAN), carbon fibers, carbon black, nano graphite platelets, or particles of the inherently conductive polymers listed above). Conductive carbonaceous material is preferred. The electrically conductive filler may be in the form of substantially spherical, flakes, fibers or any mixture thereof. Fibers are particularly preferred. Conductive carbonaceous filler may be dispersed in the resin matrix in any suitable amount that provides a desired electrical performance while maintaining processibility of the conductive thermoplastic or elastomeric resin. For many applications, an amount of conductive filler in a range of about 20-60 wt %, based on total weight of the conductive thermoplastic or elastomeric resin, may be suitable. In preferred embodiments, the amount of conductive filler may be controlled in a range of about 25-50 wt % or about 30-40 wt %.

The resin preferably comprises a sufficiently high melt-flow index to facilitate melt processing, especially extrusion, even with significant loading of conductive filler. Any suitable melt processing regime may be employed to provide the electrically conductive thermoplastic or elastomeric resin. For example, the resin may be compounded in an extruder (e.g. a single or twin screw extruder), in a kneading batch mixer or in the like, and then delivered directly to hot pressing. Alternatively, the resin may be pre-compounded in any manner suitable for creating a percolated network using one melt processing technique and then delivered to hot pressing by another technique. In one embodiment, the resin may be compounded in an extruder and extruded directly to hot pressing, although the resin does not need to be compounded in an extruder at the time of extrusion/molding.

Extrusion or other melt processing of the conductive resin is combined with hot pressing to form a film of the conductive resin. Hot pressing may comprise any suitable method, for example compression pressing or calendering, using a compression press or calender rolls, for example. The use of calendering with calender rolls is particularly preferred. At the same time as forming the film, appropriate eyelet features (e.g. posts, flanges, etc.) may be formed on or in the film to provide a web of eyelets integrally formed on or in a single film. By machining desired dimensions into one or more of the press platens or calender rolls, features may be transferred to the film simultaneous with the formation of the film. For example, cavities in one or more of the press platens or calender rolls would provide posts or other protuberances protruding from the film. Countersinks around the cavities would produce discs around a base of the posts or other protuberances in the web. Raised elements on one or more of the press platens or calender rolls would provide thinner areas in the web that may be utilized to reduce the thickness of the web that needs to be cut to produce the individual eyelets. Providing features in the film simultaneously with the formation of the film eliminates the need to later machine the eyelet to produce the same feature.

The eyelets may be provided on the web in any suitable pattern and spaced apart with any suitable spacing. For example, the eyelets may be provided in a random pattern or in a repeating pattern (e.g. rows) on the web. When the eyelets are provided in longitudinal rows with respect to a long axis of the web, the longitudinal rows of eyelets may be transversely aligned with or staggered in relation to each other. Preferably, the pattern of eyelets on the web is designed to facilitate separation of the eyelets by a cutting technique (e.g. die cutting) and/or to reduce the amount of excess resin (the ladder) after the eyelets have been separated from the web.

One hot pressing technique for providing eyelet features in film is known as extrusion replication, which is further described in U.S. Pat. No. 6,919,504 issued Jul. 19, 2005 to McCutcheon et al., the contents of which is herein incorporated by reference. In brief, when a surplus of extruded conductive resin is drop coated into the nip of calender rolls, the resin is forced into cavities and/or around features machined in the roll or rolls and solidifies into a film with a plurality of features of desired shape spaced apart in a desired pattern. A web of components on a single film of resin is formed as opposed to producing discrete components. For the production of eyelets, one of the rolls may be machined with cavities while the other remains smooth or has other features machined therein, which results in a film having a plurality of posts on a first face and a second face that is smooth or comprises other features. Each post represents a single potential eyelet and all of the potential eyelets may be coated with non-polarizable conductive material at substantially the same time by coating the second face of the film, thereby coating the contact faces of the respective flanges associated with each post. Applying non-polarizable conductive material on only the contact face of the eyelet is thereby made much easier by the present process. However, in some cases it may be desirable to coat the contact faces of the eyelets after separation of the eyelets from the web.

Extrusion replication to form a web of eyelets opens the possibility of using a wide variety of coating techniques to apply the non-polarizable conductive material to the web of eyelets. Coating techniques may include, for example, ink printing (e.g. screen printing, inkjet printing, flexography printing, gravure printing, off-set printing, airbrushing, aerosol printing, typesetting and the like), simultaneous feeding of pre-coated films or liners to transfer non-polarizable conductive material to the resin film, thermally embedding particles of non-polarizable conductive material or particles coated with non-polarizable conductive material into the second face of the web, electroplating, electro-less plating, sputtering, vacuum deposition, thermal deposition and the like. Ink printing is particularly preferred. Further, coating methods used may selectively coat the non-polarizable conductive material only on the required area, which reduces overall process cost as less non-polarizable conductive material is required, and in a preferred embodiment, simultaneous extrusion and coating reduces the number of process steps thereby reducing overall process cost.

The process is flexible enough to accommodate a variety of non-polarizable conductive material including inks, coated particles, pure material and the like. The non-polarizable conductive material preferably comprises a non-polarizable conductive metal-containing material. The metal in the metal-containing material preferably comprises silver or iron. In a preferred embodiment, the non-polarizable conductive material includes silver inks, silver-coated particles, silver metal and the like. The non-polarizable conductive material may be provided in different forms, for example as a liquid, a pre-formed film and the like, since the extrusion replication process permits multiple methods for applying the non-polarizable conductive material to the film.

Inks comprise particles (e.g. nanoparticles, flakes) dispersed in a solvent usually with a binder. The solvent may comprise an aqueous solvent or an organic solvent (e.g. benzene, toluene, ethylbenzene, xylenes, chlorobenzene, benzyl ether, anisole, benzonitrile, pyridine, ethylbenzene, propylbenzene, cumene, isobutylbenzene, p-cymene, indane, tetralin, trimethylbenzenes (e.g. mesitylene), durene, p-cumene, indane, tetralin or any mixture thereof) and the binder generally comprises a polymeric material (e.g. ethyl cellulose, hydroxypropyl cellulose, hydroxymethyl cellulose, hydroxyethyl cellulose, polypyrrolidone, polyvinylpyrrolidones, epoxies, phenolic resins, acrylics, urethanes, silicones, styrene allyl alcohols, polyalkylene carbonates, polyvinyl acetals, polyesters, polyurethanes, polyolefins, fluoroplastics, fluoroelastomers, thermoplastic elastomers or any mixture thereof).

Particles coated with the non-polarizable conductive material may be of any suitable composition, shape and size. For example, the particles may comprise glass, plastic resin (e.g. thermoset or thermoplastic resins), quartz, or the like. Glass particles are preferred. The particles may be solid or hollow. The particles may be substantially spherical (e.g. beads), flakes, fibers, or the like. The particles preferably have an average size of about 500 μm or less, more preferably in a range of about 1-300 μm, more preferably in a range of about 2-200 μm. Substantially spherical particles preferably have an average particle diameter in a range of about 4-100 μm. Flakes and fibers preferably have a longest dimension in a range of about 50-200 μm, more preferably in a range of about 75-150 μm. The particles preferably comprise about 1-50 wt % silver based on total weight of the particles, more preferably about 2-40 wt %, more preferably about 4-30 wt %. Mixtures of particles having different compositions, shapes and/or sizes may be used to further control performance properties of the electrode.

Some types of electrodes require the non-polarizable conductive material component to be partially converted to an ionic state in order to function, for example in order to interact with different electrolyte gels. Where the non-polarizable conductive material comprises a metal-containing material, elemental metal in the non-polarizable metal-containing material may be partially oxidized. The non-polarizable metal-containing material would then comprise metal in the 0 oxidation state along with one or more cations of the metal. In the case of silver, the silver may be pre-chlorinated to produce some $Ag^+$ ions in the silver-containing material. In such applications, a coating of silver-containing material may be partially pre-chlorinated to provide a mixture of silver (Ag) and silver chloride (AgCl) in the layer. Chlorination of the silver may be accomplished by any suitable method, for example by reacting the silver with a chlorinating agent. Chlorinating agents include, for example, chlorite ($ClO_2^-$). The silver may be chlorinated to provide a desired ratio of silver to silver chloride provided there is sufficient silver remaining for the desired function and performance. Alternatively or additionally, a commercially available silver/silver chloride ink can be coated onto the smooth portion of the web. This removes the need for chlorinating the printed silver, for example as described in U.S. Pat. No. 4,377,170 published Mar. 22, 1983, the contents of which is herein incorporated by reference. In the case of iron, the iron may be partially oxidized to iron (II) and a counterion anion (e.g. sulfate) used to balance the charge. A mixture of iron (Fe) and ferrous ions (e.g. in the form of ferrous sulfate ($FeSO_4$)) would be present in the layer.

Further, residual heat of the melt processed resin may be utilized to dry and sinter inks eliminating the need for drying ovens and further steps associated therewith, and pressure applied during hot pressing helps adhere the ink to the film. The residual heat from melt processing and pressure from the hot pressing may be used to thermally embed particles coated with the non-polarizable conductive material into a still soft resin film to form a layer of particles coated with non-polarizable conductive material anchored to the film. In both cases, utilization of residual heat and pressure in the process increases robustness of the coating.

Individual eyelets may be separated from the eyelet web by cutting, preferably die cutting, although any cutting method may be employed. The eyelets may be separated at any time in the process after the web is formed. For example, the non-polarizable conductive material may be applied on to the second face of the film and the film then cut to produce the separated eyelets, wherein the flange of each eyelet comprises a contact face coated with the non-polarizable conductive material and the post of each eyelet is not coated with the non-polarizable conductive material. Alternatively, the film may be cut to produce an eyelet without non-polarizable conductive material, the eyelet comprising a post and a flange with a contact face, and then the non-polarizable conductive material applied on to the contact face of the flange. In a preferred embodiment, the eyelets are separated from the web after the non-polarizable conductive material is applied to the film. However, it is possible to cut a web of eyelets not coated with non-polarizable conductive material to produce individual eyelets not coated with non-polarizable conductive material, each eyelet having a post and a flange with contact face, and then applying the non-polarizable conductive material to the contact faces, and possibly to any other desired portion of the eyelet. Applying the non-polarizable conductive material before cutting is simpler, providing a more streamlined and cost-efficient process. However, if cut edges are too rough or contain too much debris, then applying the non-polarizable conductive material after separating the eyelets may be advantageous because alternative processes like tumbling or deburring may be enabled without removing the coating of non-polarizable conductive material. Further, separating the web may also reduce wastage of the non-polarizable conductive material because coating after cutting would provide the non-polarizable conductive material only on the contact faces themselves and not on material that would be cut out and removed (i.e. the ladder). By not applying non-polarizable conductive material on the ladder, the cost of the non-polarizable conductive material would go down, which is especially useful when the non-polarizable conductive material comprises a silver-containing material. However, reducing the amount of non-polarizable conductive material may also be accomplished by pattern coating the non-polarizable conductive material on the second face of the web before cutting. Alternatively, the eyelets may be separated and collected for coating later (such as for electroplating) or use them in electrode constructions that do not need an eyelet coated with non-polarizable conductive material (e.g. an offset electrode).

Where fibrous conductive fillers are dispersed in the conductive resin, the extrusion replication process advantageously orients the fibers in the resin in a direction parallel to the surface of the film. Because the eyelets are produced form a web, the fibers at the edge of the contact face are oriented perpendicular to the edge (parallel to the contact face). Further, where the posts are formed due to cavities in the calender roll, the conductive fibers in the bulk of the posts are oriented perpendicular to the plane of the film (i.e. parallel to the direction the post protrudes). Orientation of the fibers in the above manner may provide some electrical benefit (e g enhanced percolation and/or overlap) in comparison to eyelets formed from other molding processes, such as injection molding, that result in a random orientation of fibers in the bulk of the posts.

By varying input resin, press platens or calender rolls, and silver layer thickness, a wide degree of flexibility is available to quickly tailor eyelets for a product line. For example, high-end electrodes can have higher conductivity resin and a thicker layer of non-polarizable conductive material, whereas low-end electrodes can be developed from a lower conductivity resin and a thinner layer of non-polarizable conductive material. In addition to eyelets produced for standard biomedical electrode styles, eyelets with new dimensions and geometries, that may or may not need the current mating retaining stud may be manufactured in this process. Any style of biomedical electrode may be produced with the process, for example monitoring ECG electrodes, resting (tab) ECG electrodes and the like.

Figure 1:
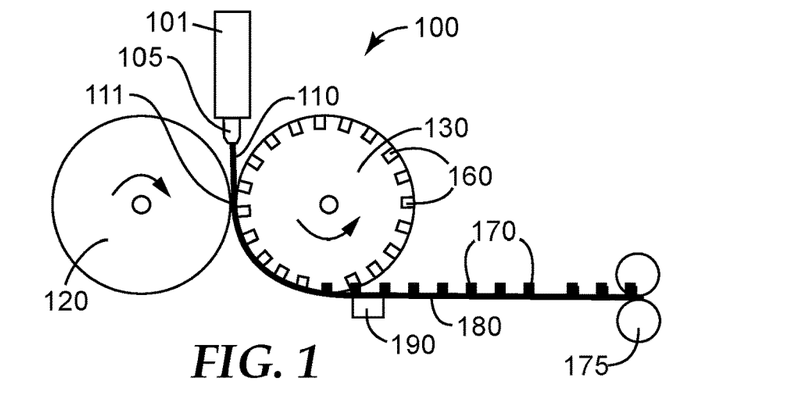
FIG. 1 depicts an extrusion/calendering arrangement for producing a web of eyelets for ECG electrodes from an electrically conductive thermoplastic or elastomeric resin, where a silver ink is applied to a face of the web with an inkjet coater in-line with the extruder and calender rolls.

Referring to FIG. 1, one embodiment of the process schematically illustrated shows a two-roll molding apparatus 100 that includes an extruder 101 with an extrusion die 105 adapted for extruding one or more layers of molten conductive resin 110 into a nip 111 between two calender rolls 120, 130. Instead of an extrusion die, any suitable structure for feeding molten conductive resin from the extruder to the nip may be employed, for example a simple tube or different kinds of dies. Calender roll 130 is a mold roll and calender roll 120 is an opposed roll to the mold roll 130. The mold roll 130 has on its outer cylindrical surface a desired surface pattern for transference to the molten resin 110 as the resin 110 passes over the cylindrical surface of the mold roll 130. The surface of mold roll 130 has a plurality of arranged cavities 160 adapted to form a plurality of posts 170. The cavities 160 may be arranged, sized, and shaped as desired to form suitably sized and shaped posts 170 from conductive resin 110. The mold roll 130 is rotatable and along with the opposed roll 120 forms the nip 111. This nip 111 assists in flowing molten resin 110 into the cavities 160 on the mold roll 130. The width of nip 111 can be adjusted to assist the formation of a selected thickness of the web 180. The temperatures of the rolls 120, 130 may be independently and selectively controlled to achieve desired cooling of the resin 110.

When making the mold roll 130 for forming posts 170, cavities 160 of mold roll 130 may be formed in any suitable manner, such as one or more of chemical, electrical, and mechanical machining or forming processes. Examples include drilling, machining, laser drilling, e-beam drilling, water jet machining, casting, etching, die punching, diamond turning, engraving knurling, and the like. The cavities 160 may alternatively be formed by providing a suitably patterned exterior polymeric wrap around the mold roll 130. The surface of the mold roll 130 may also include a release coating thereon selected to facilitate release of the web 180 from the mold roll 130. The flow of molten resin 110 into mold roll 130 and cavities 160 may be controlled by the application of pressure between opposing roll 120 and mold roll 130, by the temperature of the molten resin 110, by the quantity of resin 110 in the nip 111, by extruder flow rates in conjunction with the line speed of the cavities 160 and/or by evacuating the cavities 160 before applying the resin 110.

After the molten resin 110 has been coated in cavities 160 and over the surface of mold roll 130, the resin is cooled to solidify and form the web 180 with desired exterior surface topography (e.g. the posts 170) thereon. The web 180 is then separated from mold roll 130. The web 180 often will shrink slightly when cooled and solidified, which facilitates release of the web 180 the mold roll 130. Part or the entire mold roll 130 may be cooled to aid in solidifying the web 180. Cooling can be effected directly or indirectly via any known means such as using water, air, other heat transfer fluids, or other cooling processes. An ink (e.g. a silver ink) is applied to a surface of the web 180 opposite the surface with the posts 170 by ink jet printing at an inkjet printing station 190.

Figure 2:
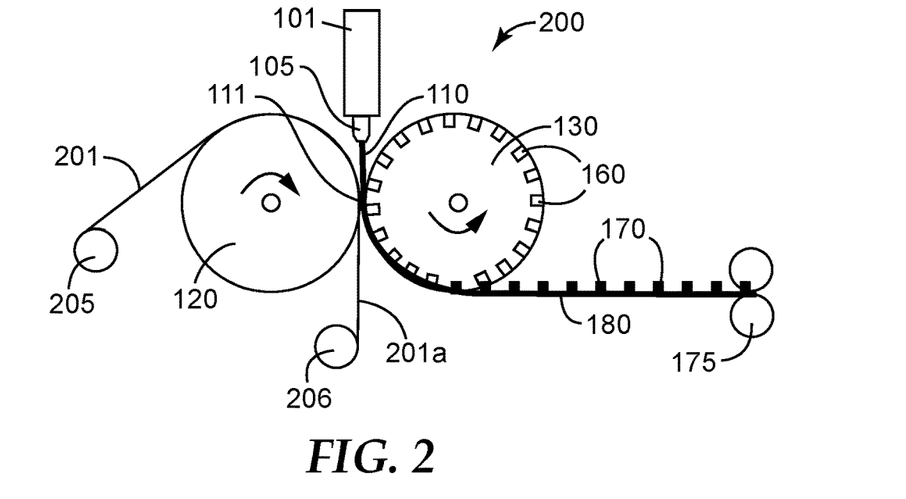
FIG. 2 depicts an extrusion/calendering arrangement for producing a web of eyelets for ECG electrodes from an electrically conductive thermoplastic or elastomeric resin, where a layer of silver-containing material is applied to a face of the web simultaneously with the formation of the web from a pre-prepared solid silver-containing film.

Referring to FIG. 2, another embodiment of the process schematically illustrated shows a two-roll molding apparatus 200 that works similarly to the apparatus 100 depicted in FIG. 1 except that coating silver-containing material on the web 180 is accomplished simultaneously with formation of the web 180. A pre-prepared solid silver-containing film 201 (e.g. a liner comprising a coating of silver-coated particles adhered thereto or a silver ink printed thereon) is threaded through the nip 111 together with the molten resin 110 between the molten resin feed and the opposed roll 120. Under pressure from the calender rolls 120, 130, the silver-containing material is transferred from the silver-containing film to the smooth face of the web 180 as the web 180 is being formed. The posts 170 are formed on the opposite face of the web 180 in contact with the mold roll 130. The pre-prepared solid silver-containing film 201 is fed through the nip 111 using a roll-to-roll device comprising a feed roll 205 and an uptake roll 206, the uptake roll 206 winding up the silver-less film 201a after transfer of the silver-containing material to the web 180. This embodiment permits continuous formation and silver coating of a web of eyelets on only one side of the eyelet all in one step.

Figure 3:
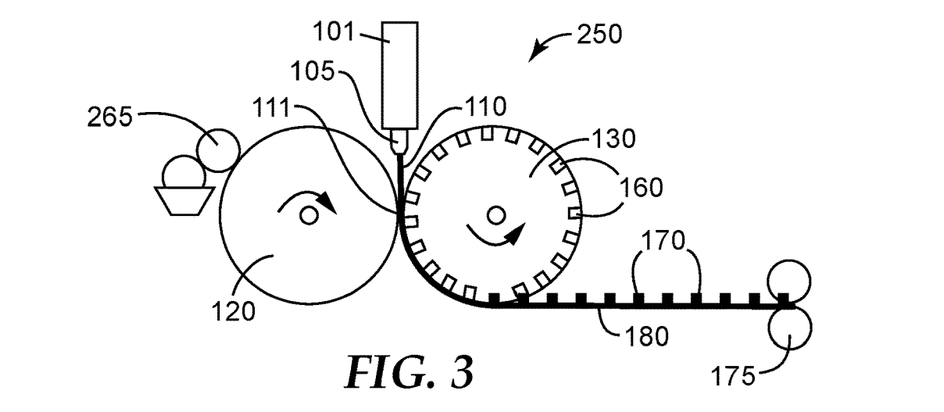
FIG. 3 depicts an extrusion/calendering arrangement for producing a web of eyelets for ECG electrodes from an electrically conductive thermoplastic or elastomeric resin, where a layer of silver-containing material is applied as a liquid silver ink to a face of the web simultaneously with the formation of the web.

Referring to FIG. 3, another embodiment of the process schematically illustrated shows a two-roll molding apparatus 250 that works similarly to the apparatus 200 depicted in FIG. 2 except that coating non-polarizable conductive material (e.g. silver-containing material) on the web 180 at the nip 111 is accomplished by flexographically printing a liquid ink on to the opposed roll 120 at a flexographic printing station 265. The ink is transferred from the opposed roll 120 to web 180 as the web 180 forms in the nip 111. Applying liquid ink in this fashion provides all of the benefits of transferring a dried pre-printed film as illustrated in FIG. 2 without using and disposing of a liner. The liquid ink dries/sinters and becomes a solid, thermally embedded layer all at the nip 111. Instead of flexographically printing the ink on to the opposed roll 120 as illustrated in FIG. 3, other printing techniques may be used, for example inkjet printing, screen printing or spray printing.

Once the web 180 of eyelets has been formed and coated with the non-polarizable conductive material, individual eyelets may be separated from the web by cutting at a cutting station 175, inspected and tested, and packaged for delivery or assembled into electrodes. Cutting may be performed before or after inspection and/or testing.

Figure 4:
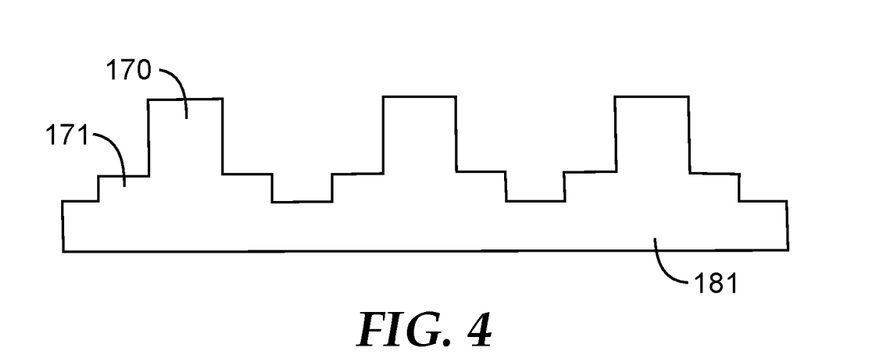
FIG. 4 depicts one embodiment of a web of eyelets that may be produced by a process for producing a web of eyelets.
Figure 5:
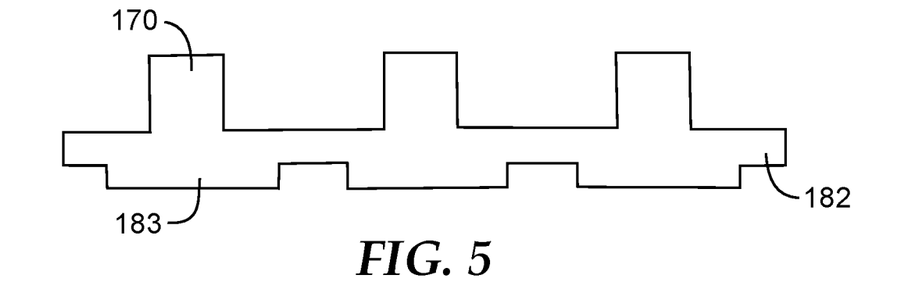
FIG. 5 depicts another embodiment of a web of eyelets that may be produced by a process for producing a web of eyelets.

FIG. 1, FIG. 2 and FIG. 3 illustrate processes in which the opposed roll 120 is smooth thereby producing a smooth second face of the web 180, and the mold roll 130 only has cavities 160 designed to produce simple posts 170 on the first face of the web 180. However, in other embodiments, one or both of the opposed roll and the mold roll may comprise further features machined therein to produce various other desired eyelet features. For example, with further reference to FIG. 4, countersinks machined out of the mold roll 130 around the cavities 160 would produce a web 181 comprising discs 171 around the base of the posts 170 on the first face of the web 181, thereby eliminating the need to later machine the eyelet to produce the same feature. In another example, with further reference to FIG. 5, the opposed roll 120 may contain machined features to provide a portion 183 of the final eyelet on the second face without needing to further cut the web 182 to provide the portion 183. This reduces overall thickness of the web 182 and the thickness of web that needs to be cut to produce the individual eyelets. Where features are produced on the second face of the web, applying the non-polarizable conductive material (e.g. silver-containing material) using a solid liner during web formation as illustrated in FIG. 2 may be problematic due to the non-smooth second face, but applying the non-polarizable conductive material as a liquid after web formation as illustrated in FIG. 1 is still enabled.

The eyelets may be assembled into electrodes, especially electrodes for electrocardiography (ECG), together with other electrode components. The electrode may be of any style in which a surface coated with non-polarizable conductive material is applicable, for example monitoring ECG electrodes, resting (tab) ECG electrodes, electromyography (EMG) electrodes, transcutaneous electrical nerve stimulation (TENS) electrodes, and the like. Specifically, ECG electrodes comprise the eyelet and one or more other components including, for example, a conductive gel or adhesive, a foam layer, a backing, one or more studs and a cover. As described above, the eyelet comprises a contact face through which electrical signals are received from the subject's skin. To enhance electrical contact between the subject's skin and the contact face of the eyelet, the electrode may further comprise a conductive gel or adhesive that act as a conformable conductive interface between the eyelet and the subject's skin. In the case of a conductive adhesive, the adhesive also helps secure the electrode to the skin. Where a gel or adhesive is used, the electrode may comprise a removable cover to protect and contain the gel or adhesive before use. A foam layer surrounding or absorbing the gel or adhesive may also be used to protect and contain the gel or adhesive. The cover may be removed to expose the gel or adhesive just before use. The electrode may further comprise a backing on a side of the eyelet away from the layer of silver-coated face. The backing may provide support for the eyelet and/or a convenient place to handle the electrode without damaging the eyelet and/or gel or adhesive. The backing may comprise any suitably handleable material. Polymeric backings are preferred as they have a good combination of structural strength for handling, flexibility for conforming the electrode to the subject's skin and low density for reducing overall weight. The eyelet comprises one or more posts that mate with retaining studs which act as lead terminals to which electrical leads may be attached, the electrical leads carrying electrical signal back to an output device. Electrical signals from the subject's skin are conducted through the face coated with non-polarizable conductive material (or the conductive gel or adhesive and then the face coated with non-polarizable conductive material) though the bulk of the eyelet, which comprises electrically conductive resin, through the one or more posts into the leads and thence to the output device. In some cases, one or more electrically conductive studs (e.g. made of brass, stainless steel or the like) may cover the one or more posts as a way of attaching the backing to the eyelet, but the electrode does not need the stud to function. The electrode arrangement is not particularly limited and the eyelet may be used in any of a wide variety of electrode arrangements.

In one embodiment of a complete continuous process for producing an electrode coated with non-polarizable conductive material (e.g. silver-containing material), a web of eyelets formed by hot pressing in accordance with the invention may be advanced to a coating station where non-polarizable conductive material is coated on the contact face of the eyelets, for example by coating the second face of the film. The coating station may also comprise an oven for drying and sintering the non-polarizable conductive material on the contact face of the eyelet, or the non-polarizable conductive material may be air dried and sintered in an oven downstream in the process, if desired. The web of eyelets coated with non-polarizable conductive material may then advance to a backing application station where a backing material (e.g. a polymer or foam sheet) may be applied to the first face of the film such that the posts protrude through the backing material. The backed web of eyelets coated with non-polarizable conductive material may then advance to an electrolyte application station where the coated contact faces of the eyelets are further coated with a conductive gel or adhesive using an electrolyte applicator. In embodiments where a gel is used, to facilitate retention of the gel, the backing material is preferably a foam material having wells formed therein within which the eyelets are contained. Alternatively, when using a thin web/tape as the backing material, a piece of open cell absorbing foam can be secured on top of the eyelet to contain the gel. Various suitable kinds of conductive gels and adhesives are known in the art. The gel- or adhesive-coated eyelet may then advance to a cover application station where a removable cover is applied over top of the coated contact faces of the eyelets to protect the conductive gel or adhesive during handling and to provide a seal for moisture retention of the gel. The cover may be applied by any suitable method, for example by continuously feeding the cover from a feed roll and holding the liner in contact with the second face of the film with a press roll. The cover may comprise an adhesive layer to enhance adherence of the cover to the film. Some preferred cover materials are polyethylene terephthalate (PET), high impact polystyrene and polyethylene coated paper. The covered web of eyelets may then advance to a stud fitting station where metal studs are secured over the posts to help secure the eyelets to the backing material. In this embodiment, up to the fitting of the studs, all of the eyelets are contained in a continuous web. While separation of the eyelets from the web may be done at any stage of the process, this embodiment illustrates separation of the formed electrodes after the studs are fitted, however separation may be performed, if desired, at any place in the process after forming the eyelets in the film. Separation is performed at a separation station and may be performed by any suitable method, for example die cutting with a die cutter. The separated electrodes are advanced to a packaging station where the electrodes may be packaged and/or collected, for example placed in moisture proof bags.

Figure 7:
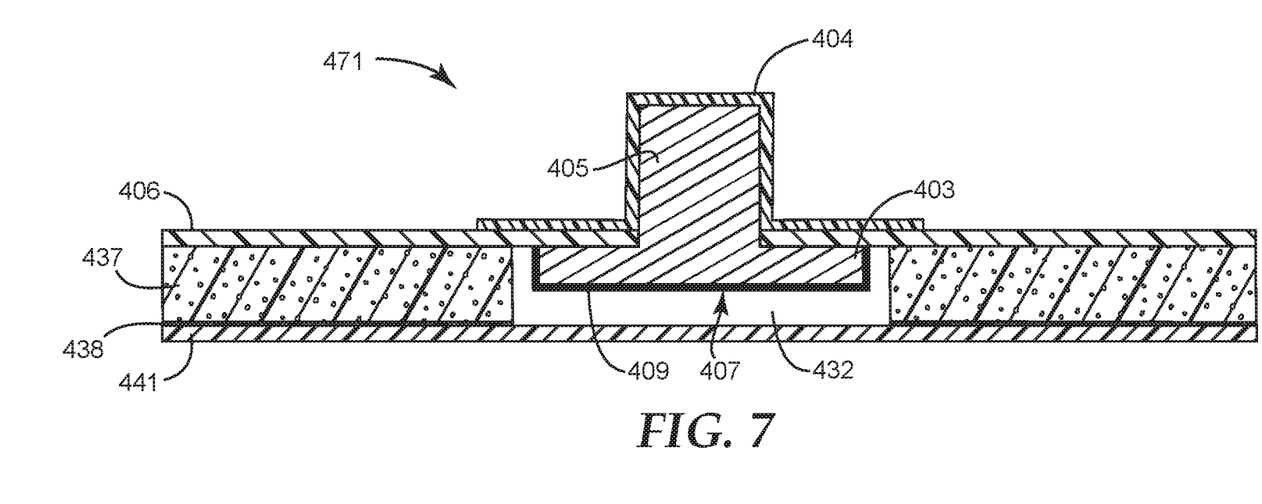
FIG. 7 depicts one embodiment of a biomedical electrode comprising an eyelet produced by a process of the present invention.

FIG. 7 depicts a side cross-sectional view of an embodiment of a fully assembled electrode 471. The electrode 471 comprises an eyelet 407 anchored in a backing material 406 by a stud 404 fitted over a post 405 of the eyelet 407 protruding through the backing material 406. The eyelet 407 further comprises a flange 403 having a contact face coated with a layer 409 of non-polarizable conductive material (e.g. silver-containing material), and the contact face is the primary surface of the eyelet 407 through which electrical impulses from a subject will be received during use of the electrode 471. The post 405 extending through the backing material 406 extends away from the backing material 406 on an opposite side of the backing material 406 from the flange 403. In contact with the layer 409 of non-polarizable conductive material is a conductive gel 432 contained within the electrode 471 at the flange 403 in a well in a closed cell foam layer 437 secured to the backing material 406. A cover 441 covers the foam layer 437 and the well in the foam layer 437 to protect and contain the conductive gel 432 and to protect a layer of skin adhesive 438 on foam layer 437.

EXAMPLES

Preparation of Electrically Conductive Resin

Conductive resin for eyelet fabrication was produced by compounding a resin matrix and a conductive filler using a twin screw extruder. If desired, the conductive filler may be surface modified to enable easy dispersion and bonding with the resin matrix. Conductive filler was added at various weight percentages into the resin matrix and electrical conductivity measured to determine that about 30 wt % conductive filler was sufficient for lower-end eyelets, while up to about 40 wt % could produce eyelets that matched or exceeded current commercial eyelets.

Example 1

Eyelet Production Using Post-Calendering Silver Application

Figure 6:
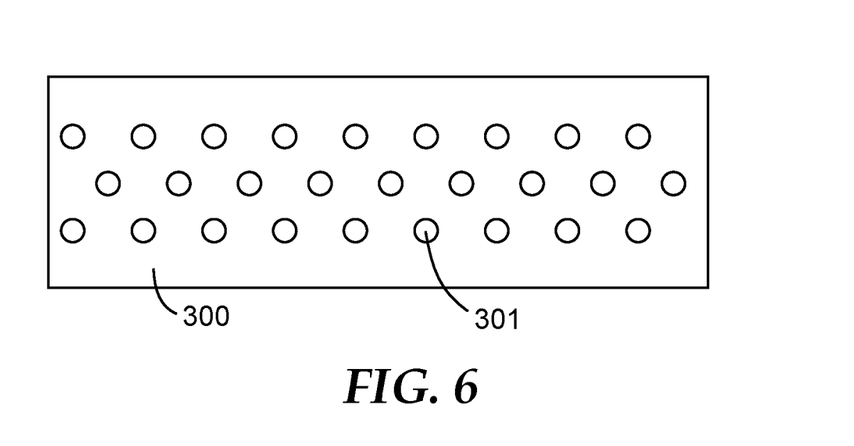
FIG. 6 depicts a schematic diagram of an eyelet post pattern punched out of a plastic sheet that was wrapped around a calender roll to enable formation of posts on a film of extruded electrically conductive resin.

Referring to FIG. 6, post cavities 301 were punched out of a stiff plastic sheet 300 using a die in varying patterns. The post cavities 301 were spaced and sized so that once cut out of the web, the eyelets so produced would have a post and contact face with the desired size for an eyelet for an ECG electrode. The sheet 300 was wrapped around one of the rolls in an extrusion/calendering arrangement similar to the one described in connection with FIG. 1 to create the posts of the eyelet web. The extrusion die was placed such that the material would be drop-coated between the calender rolls. In order to extrude enough material to fill the post cavities and create a continuous web, the extruder was run at a faster speed than the line could take it away. These processing parameters caused the material to build up slightly at the roll nip. An optimal balance was found so that the build-up was static in size and the residence time of the build-up was not significant enough that the resin started to solidify, which would have caused incomplete cavity filling and 'wavy' marks or inconsistent thickness on the web portion. Web production was conducted as described in connection with FIG. 1. The conductive resin relatively easily filled the post cavities with only a few changes to extruding parameters. Once optimized, the material completely filled all post cavities, even when spaced close together. Due to the elastic nature of the silicone sheet, some degree of variation in post diameter was observed. An aluminum sleeve with accurately dimensioned post cavities may help prevent such variations Machining the cavities directly into the calender roll may also prevent such variations.

A layer of silver on the contact face is desirable for eyelets. The flat face of the eyelet web produced above may be coated with a silver ink using a flexographic coater as described in connection with FIG. 1. The flexographic coater may be positioned close enough to the rolls that residual heat of the extruded conductive resin is enough to quickly dry and sinter the silver ink without the requirement for ovens. To avoid the possibility of clogging due to premature drying of the ink, offset printing onto a continuous belt that comes in contact with the conductive resin may be used.

For evaluation purposes, ink printing in this example was simulated off-line after extrusion and formation of the web. Electrodes were assembled using eyelets produced in this continuous manner. 8 mm diameter punches were used to cut out eyelets from the web at various locations. These eyelets were coated with liquid silver ink by hand using ACHESON ELECTRODAG PM-500 from Henkel. Electrodes were assembled as a one-piece electrode (no studs, leads connected directly to eyelets). Eyelets were placed onto LDPE tape, and a scrim was placed around the eyelet to anchor ionic gel on the eyelet face. UV curable electrolyte gel was placed on top of the eyelet and cured. These electrodes were aged at 49° C. in a moisture tight bag to allow the silver to react with the salts and convert to silver/silver chloride. After 2 days, the electrodes were removed and tested back-to-back as pairs. A commercially available eyelet (S-9129/300/SP/0.065/AG, available from Select Engineering, Fitchburg, Mass.) was assembled in the same manner and used as a reference. Testing was performed as per ANSI/AAMI EC12:2000 method TS-667. Desired performance limits are: DC Offset (DCO)=100 mV, AC Impedance (ACZ)=3000 Ohm, Simulated Defibrillation Recovery (SDR)=100 mV. The results can be seen as follows in Table 1. It is evident that eyelets produced in this Example easily complied with the desired performance limits and approached the performance of the commercially available eyelets.

TABLE 1

| Eyelet | DCO (mV) | ACZ (Ohm) | SDR (mV) |
| --- | --- | --- | --- |
| 30 wt % conductive filler | 1.6 | 253 | 11.9 |
| 35 wt % conductive filler | 0.7 | 158 | 11.8 |
| 40 wt % conductive filler | 0.5 | 98 | 11.2 |
| S-9129/300/SP/0.065/AG | 0.5 | 95 | 9.8 |

Example 2

Eyelet Production Using a Pre-Printed Film During Calendering

In this example, forming and silver coating of an extruded film of conductive resin are performed simultaneously at the roll nip to produce a silver-coated eyelet web in a one-step continuous process. A polyethylene terephthalate (PET) film was hand-coated with liquid silver ink and allowed to dry under ambient conditions to produce a pre-printed film. The pre-printed film was threaded as a liner in the extruder/calender arrangement as described in connection with FIG. 2. The liner was placed so that the silver would come in contact with the conductive resin as the resin was extruded. The conductive resin was extruded with the same parameters as in Example 1. The liner was peeled off the resin immediately after the roll nip. Contact time of the silver-coated PET film with the conductive resin was kept to a minimum. With minimal contact the silver still completely delaminated from the PET film and anchored to the conductive resin. The formation of the posts remained unaffected by the silver lamination and the thickness of the web was only marginally changed. This procedure demonstrated one-step continuous forming of a web of eyelets with a layer of silver on the contact face and posts protruding from the opposite face. A roll of the web was produced and eyelets were cut out at 8 mm diameter from various points throughout the web (labeled 'transfer' in Table 2). These eyelets were used in electrodes assembled the same way as Example 1. As a comparison, eyelets from areas that did not have silver coating were also punched out, but coated with liquid silver by hand (labeled 'After calendering' in Table 2). Testing was performed as per ANSI/AAMI EC12:2000 method TS-667. Desired performance limits are: DC Offset (DCO)=100 mV, AC Impedance (ACZ)=3000 Ohm, Simulated Defibrillation Recovery (SDR)=100 mV. The results can be seen as follows in Table 2. It is evident that eyelets produced in this Example easily complied with the desired performance limits and approached the performance of the commercially available eyelet.

TABLE 2

| Eyelet | Silver Coating | DCO (mV) | ACZ (Ohm) | SDR (mV) |
|---|---|---|---|---|
| 30 wt % conductive filler | Transfer | 0.6 | 178 | 10.2 |
| 30 wt % conductive filler | After calendering | 0.9 | 162 | 10.6 |
| S-9129/300/SP/0.065/AG | Commercial | 0.5 | 95 | 9.8 |

Example 3

Orientation of Conductive Fibers in Eyelets

Commercially available eyelets are usually produced by injection molding, which involves introducing molten resin into a cold cavity under a specific pressure. The resin enters the mold and is held until it solidifies producing a pattern of fibers that generally orient themselves randomly in the bulk of the eyelet. The orientation of the fibers near the walls of the cavity is mostly parallel to the cavity wall (perpendicular to the contact face of the eyelet). Specifically looking at the edge of the contact face of an eyelet, the fibers in this area of an injection molded eyelet are oriented very differently form the fibers in this area of an eyelet produce by the present process. In the commercial injection molded eyelets, fibers are aligned parallel to the edge because the resin contacts the cavity wall during injection molding and the pressure aligns the fibers in the perpendicular direction. Since the eyelets in the present process are produced from a web, meaning there is no mold wall or cavity, the fibers at the edge of the contact face are aligned perpendicular to the edge (parallel to the contact face).

The fibers in the post section of the eyelet are also different between the commercial injection molded eyelets and eyelets produced by the present process. In the present extrusion process, the fibers flow into the cavity from a flat extruded material and the orientation that results forms a U shape within the post. Along the walls of the cavity the fibers are oriented predominantly with the long axis of the post itself. However, closer to the center of the post, the fibers are oriented perpendicular to the long axis of the post. For the injection molded eyelets, the fibers again remain mostly randomly oriented in the bulk of the post area.

Another area where the fiber orientation is noticeably different is within the contact face itself. Extruding a material creates shear forces which tend to align particulates within the machine direction. This phenomenon is seen in the present invention where conductive fibers are uniaxially oriented within the flat portion of the contact face. Depending on point of view when viewing a cross-section of the eyelet, the fibers would have a different orientation with respect to the point of view. When viewing the contact surface from a perpendicular perspective, the fibers protrude out of the plane and are perpendicular to the cut or viewing surface. However, when viewing from a plane parallel to the fiber direction, the fibers are not at all protruding and are aligned predominantly with the cut or viewing plane. In contrast, the fibers in injection molded eyelets appear similarly oriented irrespective of the viewing plane and there would be more or less equal amounts of fibers protruding from the plane and running parallel to the plane.

Uniaxial fiber orientation within the contact face and the unique flow pattern of the fibers within the post are believed to benefit the electrical conductivity and performance of the eyelet. For verification, the same resin material was used to mold eyelets of the same dimensions as those in the previous examples, but using injection molding instead of the present process. Injection molding is widely used in the industry, and results in eyelets with random fiber orientation. The eyelets were tested as produced with no further processing. Eyelets were tested uncoated with silver, using only the conductive resin as conduction medium. Electrical resistance was measured from the base of the contact face to the top of the post. The resistance was measured using a standard ohmmeter and the results recorded by hand. The average value of 50 eyelets is shown below In Table 3. Table 3 shows a noticeable difference between the resistance values of the eyelets produced by the two processing methods. With the eyelets having identical composition, and very similar physical dimensions and shape, the performance difference can be attributed due to the different fiber orientations.

TABLE 3

| Production Method | Present Invention | Injection Molding |
|---|---|---|
| Conductive Resin | 30 wt % conductive filler | 30 wt % conductive filler |
| Average Resistance (Ohm) | 45 | 182 |
| Standard Deviation | 12 | 78 |
| Minimum Resistance (Ohm) | 23 | 102 |

The novel features will become apparent to those of skill in the art upon examination of the description. It should be understood, however, that the scope of the claims should not be limited by the embodiments, but should be given the broadest interpretation consistent with the wording of the claims and the specification as a whole.

The invention claimed is:

1. A process for producing an eyelet for a biomedical electrode, comprising:
    hot pressing an electrically conductive thermoplastic or elastomeric resin to produce a film comprising a web of eyelets, each eyelet comprising a post protruding from a first face of the film and a flange at a second face of the film;
    applying a coating of a non-polarizable conductive material on to a contact face of the flange; and,
    cutting the film to produce the eyelets separated from the web,
    wherein the film is cut to produce an eyelet free of non-polarizable conductive material, the eyelet comprising a contact face and a post, after which the non-polarizable conductive material is applied on to the contact face of the flange.

2. The process according to claim 1, wherein the non-polarizable conductive material is applied to the contact face by ink printing, electroplating, electro-less plating, sputtering, vacuum deposition or thermal deposition.

3. The process according to claim 1, wherein the conductive resin comprises conductive fibers dispersed in a thermoplastic resin matrix.

4. A process for producing a biomedical electrode comprising producing an eyelet by a process as defined in claim 1 and applying a backing material to the eyelet such that the post protrudes through the backing material.

5. The process according to claim 4, further comprising securing a stud over the post to secure the eyelet to the backing material.

6. The process according to claim 4, further comprising coating the contact face of the flange of the eyelet with a conductive gel or adhesive.

7. The process according to claim 6, further comprising applying a foam layer to contain and/or protect the conductive gel or adhesive.

8. The process according to claim 6, further comprising covering the contact face of the flange with a removable cover.

\* \* \* \* \*